United States Patent
Rogosnitzky

(10) Patent No.: US 9,254,289 B2
(45) Date of Patent: Feb. 9, 2016

(54) METHODS FOR TREATING EYE DISORDERS USING DIPYRIDAMOLE

(71) Applicant: Remedeye Inc., New Castle, DE (US)

(72) Inventor: Moshe Rogosnitzky, Kriat Ya'arim (IL)

(73) Assignee: REMEDEYE INC., Wilmington and New Castle, DE (US)

( * ) Notice: Subject to any disclaimer, the term of this patent is extended or adjusted under 35 U.S.C. 154(b) by 0 days.

(21) Appl. No.: 13/798,154

(22) Filed: Mar. 13, 2013

(65) Prior Publication Data
US 2014/0275124 A1 Sep. 18, 2014

(51) Int. Cl.
*A61K 31/519* (2006.01)
*A61K 9/00* (2006.01)
*A61K 9/08* (2006.01)

(52) U.S. Cl.
CPC ............. *A61K 31/519* (2013.01); *A61K 9/0048* (2013.01); *A61K 9/08* (2013.01)

(58) Field of Classification Search
CPC .................................................... A61K 31/519
USPC ...................................................... 514/226.1
See application file for complete search history.

(56) References Cited

U.S. PATENT DOCUMENTS

| 5,438,060 | A | 8/1995 | Miyazaki et al. | |
|---|---|---|---|---|
| 5,780,450 | A * | 7/1998 | Shade | 514/46 |
| 7,825,102 | B2 | 11/2010 | Fishman et al. | |
| 2005/0255144 | A1* | 11/2005 | Schultz | 424/428 |
| 2010/0222369 | A1 | 9/2010 | Fishman et al. | |
| 2013/0045940 | A1* | 2/2013 | Pescosolido | A61K 31/205 514/35 |

FOREIGN PATENT DOCUMENTS

| RU | 2008122978 A | 12/2009 |
|---|---|---|
| WO | PCT/US07/069440 | 12/2007 |
| WO | PCTUS09/063981 | 5/2010 |

OTHER PUBLICATIONS

Search Report in parallel prosecution of IL Application No. 225179, Dated Jun. 9, 2013, Israel.
Office Action in parallel prosecution of IL Application No. 225179, Dated Aug. 22, 2013, Israel.
Search Report in parallel prosecution of IL Application No. 225179, Dated Jun. 9, 2013, Israel—original Hebrew language and English Translation.
Office Action in parallel prosecution of IL Application No. 225179, Dated Aug. 22, 2013, Israel—Hebrew language and English Translation.
Translation validation regarding the two items above.
Podos, Effect of dipyridamole on prostaglandininduced ocular hypertension in rabbits, Invest. Opthalmol. Visual Sci., Jun. 1979, pp. 646-648.
Kaminski "Pharmacology Considerations with Your Patients Over 50" presentation at AFOS Meeting Oct. 22-23, 2012 in Phoenix AZ.
Li Pharmacological modulation of cytotoxicity and cellular uptake of anti-cancer drugs by PDE5 inhibitors in lung cancer cells. Pharm Res. Jan. 2014;31(1):86-96.
Doherty "Direct effects of selective type 5 phosphodiesterase inhibitors alone or with other vasodilators on the erectileresponse in cats" J Urol. Mar. 2001;165(3):1004-9.
Boptom "Modulation of tear film protein secretion with phosphodiesterase inhibitors" Clinical and Experimental Ophthalmology (2000) 28, 208-211.
Carlock "Pterygium: Nonsurgical Treatment Using Topical Dipyridamole—A Case Report" Case Rep Ophthalmol 2014;5:98-103.
Fishman "Pharmacology and Therapeutic Applications of A3 Receptor Subtype" Current Topics in Medicinal Chemistry 2003, 3, 463-469.
Gillespie "Inhibition and Stimulation of Photoreceptor Phosphodiesterases by Dipyridamole and M&B 22,948" Molecular Pharmacology, 36:773-781.
Bell"Introduction" (Apr. 2014) Phosphodiesterases and Their Inhibitors (Wiley; eds Liras and Bell) vol. 61; chapter 1 (pp. 1-7).
Maskovsky; Medicinal Drugs( 16th edition)Publishing House "LLC RIA New Wave" Submitted for publication on Oct. 15, 2009 N.A. Litvina (ed.) vol. No54 Cited from chapter "Drugs Impacting Blood Coagulation and Aggregation of the Thrombocytes" pp. 485-486 (original Russian provided with English translation).
International Search Report dated Jun. 19, 2014 in PCT/IB2014/059645.

* cited by examiner

*Primary Examiner* — Zohreh Fay
(74) *Attorney, Agent, or Firm* — IPAttitude Ltd.; S. Yarus

(57) ABSTRACT

The present invention discloses methods for treating eye disorders. The methods include the step of administering an effective amount of a topically-administered dipyridamole. Preferably, the topically-administered dipyridamole is formulated as a solution. Preferably, the topically-administered dipyridamole is at least one agent selected from the group consisting of: dipyridamole, and a pharmaceutically-acceptable salt thereof. Preferably, the effective amount corresponds to a concentration of at least about $10^{-5}$ molarity. Preferably, the effective amount is based on a treatment administration of at least once every other day.

8 Claims, No Drawings

METHODS FOR TREATING EYE DISORDERS USING DIPYRIDAMOLE

CROSS REFERENCE TO RELATED APPLICATIONS

This patent application claims priority under 35 U.S.C. §119 (a) to the Israel Patent Application filed Mar. 12, 2013 as IL225179, said Israel Patent Application having identical inventorship and assigned to same assignee as the present invention, which is hereby incorporated by reference in its entirety.

FIELD AND BACKGROUND OF THE INVENTION

The present invention relates to methods for treating eye disorders using dipyridamole.

As known in the art, the medical condition referred to as "dry eye" is a disorder of the tear film due to tear deficiency or excessive tear evaporation which causes damage to the interpalpebral ocular surface associated with symptoms of ocular discomfort. Currently, dry eye includes two major classes: (i) aqueous tear-deficient dry eye (ADDE), and (ii) evaporative dry eye (EDE). ADDE refers mainly to a failure of sufficient tear secretion due to lacrimal dysfunction. ADDE has two major subclasses, Sjogren's Syndrome dry eye (SSDE) and non-SS dry eye (such as in Graft-versus-Host Disease (GvHD) or in diabetes mellitus). EDE may be: (i) intrinsic, due to diseases affecting lid structures or dynamics, or (ii) extrinsic, in which ocular surface disease occurs due to some extrinsic exposure, such as topical drug preservatives, contact lens wear, pterygium, or vitamin A deficiency.

The term "corneal ulcer" usually refers to the medical condition in which the corneal epithelium, stroma, or both are lysed and deleted by the activation and hypersecretion of collagenolytic enzyme. The collagenolytic enzyme causing corneal ulcer, bacterial collagenase, and matrix metalloproteases (MMPs) are known to be involved in the ulcerative process.

The changes in the extracellular environment caused by the degradation of stromal collagen promote ulcers. Such conditions produce a vicious circle of activation of corneal stromal cells and degradation of corneal stroma.

When the bacteria are killed by antibiotics, secretion of bacterial collagenase is suppressed, and direct corneal stroma degradation due to the bacteria is suppressed. However, since most antibiotics cannot suppress activation of corneal stromal cell caused by the biological signals once transmitted from bacteria to corneal stromal cells, progression of ulcer is clinically observed from time to time.

The corneal/conjunctival diseases, including a repeated erosion of the cornea and a prolonged corneal epithelial deficiency, are associated with such disorders. The repairing process of the corneal/conjunctival epithelial disorders involves the coverage of the epithelial deficiency by the migration of corneal epithelial cells, followed by a subsequent cell division and differentiation, resulting in reconstitution of normal cornea and conjunctiva.

Corneal anesthesia and congenital corneal anesthesia usually develop into neurotrophic keratopathy. Neurotrophic keratopathy is a degenerative corneal disease induced by an impairment of the trigeminal nerve. Impairment or loss of corneal sensory innervation is responsible for corneal epithelial defects, ulcers, and perforations.

A pterygium is a non-cancerous growth that starts in the clear, thin tissue (conjunctiva) of the eye. This growth covers the white part of the eye (sclera), and extends onto the cornea. It is often slightly raised, and contains visible blood vessels. The problem may occur in one or both eyes. Pterygium may become inflamed and cause burning, irritation, or a feeling like there's something foreign in the eye. Vision may be affected if the grows extends far enough onto the cornea. There is at present no known curative treatment for pterygium other than surgery.

A pinguecula is a yellowish, slightly-raised thickening of the conjunctiva on the sclera, close to the edge of the cornea. Pingueculae typically occur on the part of the sclera that is between the eyelids, and therefore is exposed to the sun. In some cases, pingueculae become swollen and inflamed, a condition called pingueculitis. Frequently, pingueculae can lead to the formation of pterygia. There is at present no known curative treatment for pinguecula other than surgery.

Uveitis is inflammation of the middle layer of the eye, called the uvea or uveal tract. The uvea consists of the middle, pigmented, vascular structures of the eye, and includes the iris, ciliary body, and choroid. In western countries, anterior uveitis accounts for between 50% and 90% of uveitis cases, while in Asian countries the proportion drops to be between 28% and 50%.

Uveitis is estimated to be responsible for approximately 10-20% of the cases of blindness in the United States. The cause is generally infectious (bacterial or viral infection) or autoimmune. Genetic factors act as a predisposing factor for this difficult-to-treat condition.

In the prior art, dipyridamole {2,6-bis(diethanolamino)-4,8-dipiperidino-pyrimido[5,4-d]pyrimidine}, closely related substituted pyrimido-pyrimidines, and their preparation are taught by Fischer in U.S. Pat. No. 3,031,450 (hereinafter referred to as Fischer '450). Dipyridamole was introduced as a coronary vasodilator in the early 1960s, and is well known to have platelet aggregation inhibitor properties due to the inhibition of adenosine uptake. Subsequently, dipyridamole was shown to reduce thrombus formation in a study of arterial circulation of the brain in a rabbit model. These investigations led to its use as an anti-thrombotic agent. Dipyridamole soon became the therapy of choice for such applications as stroke prevention, maintaining the patency of coronary bypass and valve-replacement, as well as for treatment prior to coronary angioplasty.

In Patent Publication No. EP 0234854 B1 by Gilbard et al. (hereinafter referred to as Gilbard '854), it is suggested that cyclic cAMP functions as a second messenger for exocytosis in the lacriminal gland, and acts to increase tear secretion. cAMP is degraded by phosphodiesterases. It is therefore thought that suppressing phosphodiesterases can result in increased intracellular cAMP levels, and thus enhance tear secretion. Dipyridamole is believed to act as a phosphodiesterase inhibitor, and is thought to exert some of its cardiovascular benefits via this mechanism. However, on page 19 of Patent Publication No. WO 2007/140181 by Leung (hereinafter referred to as Leung '181), it is disclosed that there was a negligible effect on cAMP after the addition of dipyridamole in comparison to a control. Only a combination of caffeine and dipyridamole yielded the desired effect of decreasing cAMP in-vitro, which is assumed to indicate increased cellular levels of cAMP.

It would be desirable to have methods for treating eye disorders using dipyridamole. Such methods and treatment indications for would, inter alia, overcome the problems mentioned above associated with such ailments.

SUMMARY OF THE INVENTION

It is the purpose of the present invention to provide methods for treating eye disorders using dipyridamole.

In the interest of clarity, the term "eye disorder" is specifically defined for use herein to include, but not be limited to, any ailment of Scleritis, Graft-versus-Host Disease (GvHD), keratitis, corneal ulcer, corneal abrasion, snow blindness, Thygeson's superficial punctuate keratopathy, corneal neovascularization, Fuch's dystrophy, keratoconus, keratoconjunctivitis sicca (dry eye), iritis, corneal anesthesia, neurotrophic keratopathy, red eye, pink eye, keratomycosis, xeropthalmia, retinoblastoma, uveitis, pterygium, keratopathy, and pingueculae.

Furthermore, it is noted that the term "exemplary" is used herein to refer to examples of embodiments and/or implementations, and is not meant to necessarily convey a more-desirable use-case. Similarly, the term "preferred" is used herein to refer to an example out of an assortment of contemplated embodiments and/or implementations, and is not meant to necessarily convey a more-desirable use-case. Therefore, it is understood from the above that "exemplary" and "preferred" may be applied herein to multiple embodiments and/or implementations.

Dipyridamole is readily absorbed from the gastrointestinal tract, reaching peak plasma levels in humans 1-3 hours following oral administration. Peak plasma levels are dose dependent and range from about 0.5 µg/mL after a 25 mg dose to 1.6 µg/mL after a 75 mg dose. Blood levels are quite variable, possibly depending on food intake and gastrointestinal peristalsis. Ingestion on an empty stomach may result in higher blood levels. Following intravenous (IV) administration, the distribution half-life in humans is about 25 minutes, and after oral administration, is about 3 hours. When plasma levels of drug are followed for up to 60 hours after IV or oral administration of 20-50 mg, plasma levels decline tri-exponentially with half-lives of 5 minutes (IV only), 53 minutes, and about 10-12 hours. The volume of distribution is about 140 L with about 92 to 99% binding to plasma proteins, primarily alpha1-acid glycoprotein. Typical daily oral doses of dipyridamole range from 100-400 mg.

Dipyridamole is practically insoluble in water (water solubility is 8.17 mg/L (Meylan, W M ET AL. (1996))), and very soluble in methanol. This creates a challenge for finding a suitable method for ocular application in which an aqueous solution delivered via single drops is preferred.

Embodiments of the present invention provide methods and treatment indications for use in treating eye disorders using dipyridamole. It was determined that by adjusting the pH of the aqueous solution to ~6.6 (6.5-6.7), dipyridamole fully dissolves in the aqueous solution. The natural pH of tear fluid is 7.4; however, discomfort for the user will not be felt as long as the pH of the administered medication stays in the range of 6.6-7.8 (Sampath Kumar et al., "Recent Challenges and Advances in Ophthalmic Drug Delivery System," in *The Pharma Innovation*, Vol. 1, No. 4 (2012)).

Other methods may be used to achieve water solubility such as ultrasonic mixing, or dissolving dipyridamole in methanol, chloroform, acetic acid, DMSO, or other carriers in which the dipyridamole is soluble, followed by adding water or saline, and then removing all or part of the carrier. Another method may involve grinding the compound to a nano-particle size prior to mixing in water/saline. It should be noted that when preparing the more dilute Exemplary Formulations C & D described below, less acidification was required. While aqueous solutions tend to be preferred for ocular instillation, preparing the dipyridamole in an oil or cream base is another method to overcome the aqueous solubility challenge.

In accordance with aspects of the present invention, dipyridamole was found to be effective in treating ocular medical conditions when applied topically in physiological saline formulations. Topical application of dipyridamole may serve to treat dry eye caused by, for example, Graft-versus-Host Disease (GvHD), diabetes, allergic conjunctivitis, contact lens-related dry eye, and Sjorgen's syndrome.

In an exemplary embodiment of the present invention, topical dipyridamole may also be used to treat corneal ulcers resulting from, for example: viral infection, bacterial infection, fungal infection, injury resulting from wearing contact lenses, traumatic injury, and parasite infection. Moreover, topical dipyridamole may also be used for the treatment of pterygium, corneal anesthesia, and corneal neovascularization.

Therefore, according to the present invention, there is provided for the first time a method for treating eye disorders, the method including the step of: (a) administering an effective amount of a topically-administered dipyridamole.

Preferably, the topically-administered dipyridamole is formulated as a solution.

Preferably, the topically-administered dipyridamole is at least one agent selected from the group consisting of: dipyridamole and a pharmaceutically-acceptable salt thereof.

Preferably, the effective amount corresponds to a concentration of at least about $10^{-5}$ molarity.

Preferably, the effective amount is based on a treatment administration of at least once every other day.

These and further embodiments will be apparent from the detailed description and examples that follow.

DESCRIPTION OF THE PREFERRED EMBODIMENTS

The present invention relates to methods for treating eye disorders using dipyridamole. The aspects, uses, and advantages for such methods, according to the present invention, may be better understood with reference to the accompanying description.

The description is not to be taken in a limiting sense, but is made merely for the purpose of illustrating the general principles of the invention, since the scope of the present invention is best defined by the appended claims. Exemplary embodiments of the present invention are detailed below in the following exemplary formulations.

Exemplary Formulation A:

Dipyridamole eye drops were prepared as follows. 1 g of citric acid was mixed in 100 mL saline (0.9% w/v sodium chloride in sterile water) to obtain a pH of 6.7. 8.5 mg of dipyridamole was weighed, irradiated by UVB for 30 minutes for sterility, and diluted in the 100 mL saline. This solution was then filtered through a 0.22 micron filter for sterilization, resulting in a solution containing 85 mcg of dipyridamole per mL. Using a dropper, one drop (equivalent to approximately 0.05 mL) was applied to the eye.

Exemplary Formulation B:

Dipyridamole eye drops were prepared as follows. 1 g of citric acid was mixed in 100 mL saline (0.9% w/v sodium chloride in sterile water) to obtain a pH of 6.7. 4.25 mg of dipyridamole was weighed, irradiated by UVB for 30 minutes for sterility, and diluted in the 100 mL saline. This solution was then filtered through a 0.22 micron filter for sterilization, resulting in a solution containing 42.5 mcg of dipyridamole per mL. Using a dropper, one drop (equivalent to approximately 0.05 mL) was applied to the eye.

Exemplary Formulation C:

Dipyridamole eye drops were prepared as follows. 1 g of citric acid was mixed in 100 mL saline (0.9% w/v sodium chloride in sterile water) to obtain a pH of 6.7. 2.125 mg of dipyridamole was weighed, irradiated by UVB for 30 minutes for sterility, and diluted in the 100 mL saline. This solution was then filtered through a 0.22 micron filter for sterilization, resulting in a solution containing 21.25 mcg of dipyridamole per mL. Using a dropper, one drop (equivalent to approximately 0.05 mL) was applied to the eye.

Exemplary Formulation D:

Dipyridamole eye drops were prepared as follows. 1 g of citric acid was mixed in 100 mL saline (0.9% w/v sodium chloride in sterile water) to obtain a pH of 6.7. 1.0625 mg of dipyridamole was weighed, irradiated by UVB for 30 minutes for sterility, and diluted in the 100 mL saline. This solution was then filtered through a 0.22 micron filter for sterilization, resulting in a solution containing 10.625 mcg of dipyridamole per mL. Using a dropper, one drop (equivalent to approximately 0.05 mL) was applied to the eye.

Results:

Five human males suffering from GvHD-related dry eye were treated with one drop of Formulation A bilaterally twice daily. Subjective relief from the dry-eye symptoms was attained within half an hour. The patients required subsequent application twice daily. After 3 days of use, redness in the eye (or pink eye) disappeared.

Two human females suffering from diabetes-related dry eye were treated with one drop of Formulation C bilaterally twice daily. Relief from the dry-eye symptoms was attained within an hour. The patients required subsequent application twice daily. After 5 days of use, redness in the eye (or pink eye) disappeared.

A human female suffering from diabetes-related dry eye was treated with one drop of Formulation B bilaterally once every other day. Relief from the dry-eye symptoms was attained within twenty minutes. The patient required subsequent application once every other day. After 10 days of use, redness in the eye (or pink eye) disappeared. Maintenance continued with administration once every other day.

A human male suffering from a viral eye infection with corneal ulcer was treated with one drop of Formulation B bilaterally twice daily. Exudation ceased within 8 hours. The patient required subsequent application twice daily. After 4 days of use, redness in the eye (or pink eye) disappeared, and the eye was completely healed within 5 days.

A human male suffering in one eye from pterygium, with related dry eye and pink eye, was treated with one drop of Formulation B twice daily. Relief from the dry-eye symptoms was attained within one day. The patient required subsequent application twice daily. After 10 days of use, redness in the eye (or pink eye) disappeared. After 6 weeks of use, the ptyregium shrank by about half its size, and continued to decrease in size with ongoing use.

A human female suffering in one eye from pterygium, with related dry eye and inflammation, was treated with one drop of Formulation C twice daily. Relief from the dry-eye symptoms was attained within two days. The patient required subsequent application twice daily. After 8 weeks of use, the ptyregium shrank by about half its size, and continued to decrease in size with ongoing use.

A human male suffering from a deep corneal ulcer with stromal involvement in one eye was treated with one drop of Formulation A three times daily. Relief from pain and irritation was attained within 24 hours. The patient required subsequent application twice daily. After 7 days of use, the cornea had completely re-epithelialized.

Three females suffering from diabetes-related corneal anesthesia (neurotrophic keratopathy) were treated with one drop of Formulation C daily. Symptoms of corneal anesthesia began improving within 2-3 days. The patients required subsequent application twice daily. After about 3 weeks of use, the patients reported complete relief of symptoms.

One male suffering from diabetes-related neovascularization was treated with one drop of Formulation A twice daily. When examined after 4 weeks of use, the abnormal vessels were no longer visible by slit-lamp examination.

Two human males suffering from a viral eye infection with corneal abrasion (i.e., the onset of a corneal ulcer) were treated with one drop of Formulation A bilaterally twice daily. Exudation ceased within 5 hours. The patients required subsequent application twice daily. After 2-3 days of use, redness in the eye (or pink eye) disappeared, and the eyes were completely healed within 5-6 days.

A human female suffering from a corneal ulcer in one eye was treated with one drop of Formulation A twice daily. Relief from pain and irritation was attained within one day. The patients required subsequent application twice daily. After 7 days of use, the ulcer had healed completely.

Four human males suffering from diabetes-related dry eye were treated with one drop of Formulation A bilaterally twice daily. Relief from the dry-eye symptoms was attained on average within half an hour. The patients required subsequent application twice daily. After an average of one week of use, redness in the eye (or pink eye) completely disappeared.

Two females suffering from diabetes-related corneal anesthesia were treated with one drop of Formulation A daily. Symptoms of corneal anesthesia started improving within 2 days. After approximately one week of use, the patients reported complete relief of symptoms.

A human male suffering from diabetes-related neovascularization was treated with one drop of Formulation C twice daily. The patient required subsequent application twice daily. When examined after 16 days of use, the abnormal vessels were no longer visible by slit-lamp photography examination.

Six human patients suffering from GvHD-related dry eye were treated with one drop of Formulation C bilaterally twice daily. Relief from the dry-eye symptoms was attained within one hour. The patients required subsequent application twice daily. After an average of one week of use, redness in the eye (or pink eye) disappeared.

A human male suffering from anterior uveitis in both eyes was treated with one drop of Formulation C three times daily. Relief from pain was attained within three days. Blurred vision was resolved within 7 days. Inflammation appeared to be completely resolved within 14 days. The patient continued subsequent application twice daily to maintain remission.

A human male suffering from anterior uveitis in both eyes was treated with one drop of Formulation B three times daily. Relief from pain was attained within two days. Blurred vision was resolved within 14 days. Inflammation appeared to be completely resolved within 18 days. The patient continued subsequent application twice daily to maintain remission.

Three human patients suffering from GvHD-related dry eye were treated with one drop of Formulation D bilaterally twice daily. Relief from the dry-eye symptoms was attained within one hour. The patients required subsequent application twice daily. After an average of one week of use, redness in the eye (or pink eye) disappeared.

While the present invention has been described with respect to a limited number of embodiments, it will be appreciated that many variations, modifications, and other applications of the present invention may be made.

What is claimed is:

1. A method comprising the step of:
administering an effective amount of a topical dipyridamole composition for treating eye disorders affecting the lacrimal system of the eye to a subject in need thereof due to a lacrimal system eye disorder selected from the group consisting of dry eye, xerophthalmia and Sjogren's syndrome.

2. A method comprising:
   (a) identifying a subject in need of treatment for a lacrimal system eye disorder selected from the group consisting of dry eye, xerophthalmia and Sjogren's syndrome; and
   (b) topically administering an effective amount of a dipyridamole to said subject to treat said eye disorder.

3. A method according to claim 2, wherein said effective amount of dipyridamole is provided in a form selected from the group consisting of an aqueous solution, a cream and an ointment.

4. A method according to claim 3, wherein said effective amount of dipyridamole is provided as an aqueous solution with a pH ≤6.7.

5. A method according to claim 2, wherein said administering comprises:
   administering the effective amount of dipyridamole at a treatment frequency until symptoms abate; and
   administering the effective amount of dipyridamole at a maintenance frequency thereafter;
   wherein said maintenance frequency is lower than said treatment frequency.

6. A method according to claim 2, comprising increasing the concentration of dipyridamole according to tolerance of said subject.

7. A method according to claim 2, wherein dipyridamole is the sole active ingredient administered.

8. A method according to claim 1, wherein dipyridamole is the sole active ingredient in said composition.

* * * * *